(12) United States Patent
Khan

(10) Patent No.: US 11,109,935 B2
(45) Date of Patent: Sep. 7, 2021

(54) DISPOSABLE CONTAINER FOR SURGICAL INSTRUMENTS

(71) Applicant: HPC Healthline UK Limited matter, Morden (GB)

(72) Inventor: Fuad Khan, Morden (GB)

(73) Assignee: HPC Healthline UK Limited, Morden (GB)

( * ) Notice: Subject to any disclaimer, the term of this patent is extended or adjusted under 35 U.S.C. 154(b) by 149 days.

(21) Appl. No.: 16/090,498

(22) PCT Filed: Mar. 29, 2017

(86) PCT No.: PCT/GB2017/050885
§ 371 (c)(1),
(2) Date: Oct. 1, 2018

(87) PCT Pub. No.: WO2017/168152
PCT Pub. Date: Oct. 5, 2017

(65) Prior Publication Data
US 2019/0110852 A1    Apr. 18, 2019

(30) Foreign Application Priority Data
Mar. 29, 2016   (GB) ...................... 1605264

(51) Int. Cl.
*A61B 50/33*   (2016.01)
*A61B 50/00*   (2016.01)
(Continued)

(52) U.S. Cl.
CPC .............. *A61B 50/33* (2016.02); *A61B 50/00* (2016.02); *A61L 2/07* (2013.01); *A61L 2/206* (2013.01);
(Continued)

(58) Field of Classification Search
CPC ......... A61B 50/00; A61B 50/33; A61B 50/36; A61B 2017/0023; A61B 2050/005;
(Continued)

(56) References Cited

U.S. PATENT DOCUMENTS 3,817,420 A   6/1974 Heisler
4,193,496 A   3/1980 Barratt
(Continued)

FOREIGN PATENT DOCUMENTS

EP   0308900 A2   3/1989
EP   2543330 A1   1/2013
(Continued)

*Primary Examiner* — Bryon P Gehman
(74) *Attorney, Agent, or Firm* — Dinsmore & Shohl LLP

(57) ABSTRACT

A single use disposable container for surgical instruments is provided for transporting sterile instruments to the point of use. The single use container comprises a base section having a base and an upstanding wall extending from the base. A lid section is provided that is configured to close the base section. The container is formed from a biodegradable thermoformed pulp material that is gas and steam permeable. At least the base section includes a surfactant proof barrier on at least the inner surface of the pulp material to protect the pulp material of the container from cleaning fluid applied to the instruments. The lid includes a double walled rim that assists in protecting the instruments stored therein.

13 Claims, 3 Drawing Sheets

(51) Int. Cl.

| | | |
|---|---|---|
| *A61L 2/07* | (2006.01) | |
| *A61L 2/20* | (2006.01) | |
| *A61L 2/28* | (2006.01) | |
| *A61B 50/30* | (2016.01) | |
| *A61B 50/36* | (2016.01) | |
| *A61B 17/00* | (2006.01) | |

(52) U.S. Cl.
CPC ............... *A61L 2/28* (2013.01); *A61B 50/36* (2016.02); *A61B 2017/0023* (2013.01); *A61B 2050/005* (2016.02); *A61B 2050/0053* (2016.02); *A61B 2050/0082* (2016.02); *A61B 2050/3005* (2016.02); *A61B 2050/3008* (2016.02); *A61L 2202/17* (2013.01); *A61L 2202/182* (2013.01); *A61L 2202/24* (2013.01)

(58) Field of Classification Search
CPC .... A61B 2050/0053; A61B 2050/0082; A61B 2050/3005; A61B 2050/3008; A61L 2/07; A61L 2/206; A61L 2/28; A61L 2202/17; A61L 2202/182; A61L 2202/24
USPC ................ 206/363–370; 220/810–849
See application file for complete search history.

(56) References Cited

U.S. PATENT DOCUMENTS

| | | | | |
|---|---|---|---|---|
| 5,031,768 | A | * | 7/1991 | Fischer .................. A61B 50/36 206/370 |
| 5,372,787 | A | * | 12/1994 | Ritter ........................ A61L 2/26 206/363 |
| 6,042,000 | A | * | 3/2000 | Kawamoto .......... B65D 43/162 220/839 |
| 8,685,068 | B2 | * | 4/2014 | Sixto ...................... A61B 50/30 206/363 |
| 2010/0154353 | A1 | | 6/2010 | Cesa et al. |
| 2010/0155289 | A1 | | 6/2010 | Nazareth et al. |
| 2012/0168338 | A1 | | 7/2012 | Wu et al. |
| 2013/0105344 | A1 | | 5/2013 | Hartley |

FOREIGN PATENT DOCUMENTS

| | | |
|---|---|---|
| GB | 2474272 A | 4/2011 |
| GB | 2483133 A | 2/2012 |
| WO | 2010046617 A1 | 4/2010 |
| WO | 2014152615 A2 | 9/2014 |
| WO | 2015019061 A1 | 2/2015 |

* cited by examiner

DISPOSABLE CONTAINER FOR SURGICAL INSTRUMENTS

CROSS-REFERENCE TO RELATED APPLICATIONS

This application is the U.S. national stage of PCT/GB2017/050885 filed Mar. 29, 2017, which claims priority of United Kingdom Patent Application 1605264.9 filed Mar. 29, 2016 of which is hereby incorporated by reference in its entirety.

FIELD OF THE INVENTION

The present invention relates to a single cycle disposable container for surgical instruments, and in particular a moulded pulp fibre container.

BACKGROUND OF THE INVENTION

Surgical procedures typically require the use of a multitude of instruments, many of which are re-usable. Following surgery the re-usable instruments must be cleaned before being stored for further use. Hospitals that conduct surgical procedures therefore include in-house departments which are responsible for cleaning, storing, sterilising and transporting surgical instruments to the operating theatre for surgery. These Sterile Processing Departments typically employ reusable plastic or metal trays and containers for organising, sterilising and transporting the instruments required for a particular surgery. More recently these departments have extended their coverage area from in-house operating theatres to also include local clinics, and surgery centres. There also exists an increasing in-house demand as pressure grows within health services to do more with less.

More invasive surgeries often require large numbers of instruments which are sterilised and transported in reusable trays and containers.

Several problems occur when instruments are transported in larger containers in this manner. The first is damage. Heavy instruments collide with lighter or more delicate ones as they are being transported to and from theatre causing damage. This may jeopardise the surgery if the instruments are not suitable for use when they arrive at theatre. Furthermore, some surgical instruments may cost thousands of pounds, and any damage therefore leads to a significant financial loss for the hospital. Secondly, and of even greater concern is cross infection. Transporting instruments from many surgeries in a bulk container has in several documented cases been found to lead to cross infection amongst instruments.

It is common for individual or small groups of instruments to travel in sterilization peel pouches that are not contained in a wrapped tray or closed container system, which are methods of maintaining sterility. This is most common when sterile instruments are being transported to clinics within the hospital i.e., labor and delivery, wound care, dermatology, podiatry etc. Maintaining a rotation of reusable containers is more difficult in these clinics as compared to the OR suites. These instruments are traveling and without structural support of a tray exposes what are often very expensive and delicate instruments to damage and downtime due to instrument failure. In addition, there are patient safety concerns associated with this practice. Sterile instruments, often with sharp edges, traveling in peel pouches may puncture the pouch and compromise the instruments sterility. Often, the hole or tear is small and goes undetected and compromises the instruments sterility. Having the peel pouch travel in the single cycle container prevents damage to the sterile barrier.

It is also known for contaminated instruments to be transported in an uncontained manner, such as on open trays or bowls, between the point of use, which may for example be from a procedure room, to the Sterile Processing Department. This practice leads to the risk of the spread of infection and worker exposure from the open instruments. Therefore, in addition to the need to protect the instruments in transit, there is also a need to ensure that the instruments are containerised to prevent the spread of infection. However, the requirement for transport containers increases the burden on the wash and sterilisation facilities as the containers must also be washed and sterilised before further use. In addition, the requirement for clean trays to carry instruments can cause a bottleneck in the supply of instruments if sufficient sterilised trays are not available.

It is also important that containers for surgical instruments are clearly marked to indicate the 'sterile' or 'contaminated' condition of the instruments contained therein. Of particular importance is that used instruments are provided with a biohazard label. Re-usable containers may be marked for use with sterile instruments, or contaminated instruments, but they cannot both. Therefore, a first container including a sterile indicator must be used to transport the containers to the point of use, and a separate container having a biohazard indicator must be used for return transport. Each procedure therefore requires two separate sets of containers.

It is therefore desirable to provide an improved storage container for medical instruments which addresses the above described problems and/or which offers improvements generally.

SUMMARY OF THE INVENTION

According to the present invention there is provided a single use disposable container for surgical instruments as described in the accompanying claims.

In an aspect of the invention there is provided a single use disposable container for surgical instruments that is used to isolate instruments and prevents damage and cross infection during transport. The container is able to be used for the delivery and return of instruments from theatre or other procedure location.

In an embodiment of the invention there is provided a single use disposable container for surgical instruments. The container comprises a base section comprising a base and an upstanding wall extending from the base, and a lid section configured to close the base section. The term 'single use' or 'single cycle' refers to the use of the container for a single cycle, which may comprising transporting the sterile instruments to the point of use and then to the Sterile Processing Department following use. A single cycle may alternatively comprise the container being provided at the point of use to receive the contaminated instrument and transporting the instrument from that point to the Sterile Processing Department or other destination. During a single cycle a container is only used with one instrument or set or instruments, and is not re-used with further instruments.

The container is preferably formed from a thermoformed pulp material. Plastic or metal containers that are compatible with the high temperatures of steam sterilization make them too expensive for single use. Forming the container from a pulp material enables the container to be disposed of once the instrument is received at the Sterile Processing Department, thereby obviating the requirement to wash, sterilise or otherwise process the container. The pulp material is also advantageously biodegradable, thereby minimising the environmental impact of the containers. The pulp material is also gas and steam permeable, enabling the containers to be used to house the bagged instruments during an autoclave or gas sterilisation process prior to use.

Preferably at least the base section includes a surfactant proof barrier on at least the inner surface of the pulp material. Following a procedure surgical instruments are placed into a container and a spray of cleaning solution is applied to alleviate the problem of blood and other bodily fluids congealing and sticking to the instruments. The solution is typically a detergent and may be an enzymatic solution. However, such a spray may cause softening and weakening of a pulp container. This may lead to failure of the container or to the instruments beginning to pierce the container from the inside, thus increasing the risk of percutaneous injuries from a sharp instrument such as a skin hook. The use of a surfactant proof barrier of the inner surface of the pulp container enables the container to withstand spray application without compromising the integrity of the pulp. The pulp also includes a sizing agent to water proof the pulp.

The inner surface of the base and the inner surface of the lid may include a surfactant proof barrier.

The surfactant proof barrier may include a fluorocarbon. The fluorocarbon may be applied to the pulp within the slurry and/or may be applied to the pulp post-forming such as by spray application.

The surfactant proof barrier may include a coating of surfactant proof resin. The surfactant proof resin is preferably applied to at least the inner surface of the base prior to thermoforming. The hot press process of thermoforming advantageously allows the resin to flow between the pulp fibres immediately beneath the coated surface of the of the pulp creating a continuous surface layer of resin that completely fills and seals the surface providing improved surface finish and surfactant proofing. It has also been found to advantageously provide alcohol proofing, which enables the container to withstand alcohol based solutions resident on the instruments or applied to the instruments within the container.

The upstanding wall of the container is preferably extending from the base and has a securing lip defined around its upper edge. The lid is configured to close the enclosure, and is hingedly connected to an upper edge of the upstanding wall. The lid includes a roof, an inner wall extending downwardly from the roof, and outer wall extending upwardly from the base of the inner wall, and a securing lip at the upper end of the outer wall configured to secure over the securing lip of the base. When the lid is in the closed position the base of the inner and outer walls is located within the enclosure at a position below the securing lip with the outer wall being seated against the inner surface of the upstanding walls of the enclosure. This arrangement enables the lid to secure firmly to the base section through the engagement between the outer wall and the wall of the enclosure. In addition, the double walled arrangement provided by the inner and outer walls of the lid structurally reinforce the enclosure to protect the instrument contained therein.

The container is preferably formed from a moulded pulp material and the lid and the enclosure are integrally moulded. Preferably the moulded pulp material is thermoformed pulp. The pulp material enables the container to be single use and may be disposed of for example in a macerator. In addition the pulp material is gas porous.

The hinge is preferably a living hinge and the hinge is integrally moulded with the lid and the enclosure.

The upstanding wall of the enclosure includes two side walls and two end walls. The upstanding wall preferably tapers outwardly in the upward direction towards its upper edge. Furthermore, the outer wall of the lid preferably tapers outwardly away from the inner wall in the upwards direction at substantially the same angle as the upstanding wall of the base. This enables the outer wall to nest against the inner surface of the upstanding wall when the lid is closed. As such the lid seats securely in the enclosure, and the wall to wall contact assists in holding the lid and enclosure together.

Preferably the inner wall tapers outwardly away from the inner wall in the downwards direction towards its base, such that the outer wall and inner wall are spaced from each other.

The upstanding wall curves downwardly in the outwards direction at its upper edge to define the securing lip. The securing lip provides a substantive surface for engagement with the lid.

Preferably a flange extends horizontally outwards from the distal end of the securing lip of the enclosure. A flange may also extend horizontally outwards from the distal end of the securing lip of the lid and is arranged to seat on top of the flange of the enclosure when the lid is closed.

The enclosure is preferably formed from a gas permeable material which enable a sterilising gas such as steam or ETO (ethylene oxide) to penetrate to the interior to sterilise the instrument contained therein.

In another aspect of the invention there is provided a method of sterilising a surgical instrument comprising:
  sealing a surgical instrument within a sterilising bag;
  placing the sterilising bag containing the instrument within an enclosure according to any preceding claim; and
  placing the enclosure containing the instrument into a steriliser an exposing the enclosure to a sterilising gas such that said gas permeates the enclosure and sterilises the instrument contained therein.

This method enables the instrument to be sterilised within the container, such that it may be removed from the steriliser and handled safely and transported without contaminating the instrument, with the instrument also being protected from damage. The term "gas" includes gas phase liquids and in particular includes steam such. Where steam is used it may be generated by an autoclave process.

The enclosure is preferably closed when the instrument is placed and the enclosure is placed into the steriliser in the closed condition. This ensures the interior of the container remains secure and sterile.

The sterilised instrument is preferably transported to a point of use within the closed enclosure.

The method preferably further comprises returning the instrument to the enclosure following use and providing the enclosure with an indicia indicating the contents of the enclosure are contaminated.

One embodiment of the invention is a disposable clamshell container that isolates instruments and prevents damage and cross infection during transport; as it can be used for the delivery and return from theatre. Such a container has to be able to be sterilisable through steam, offer a positive opening and closure mechanism and protect the instruments.

In another aspect of the invention there is provided a method of transporting a contaminated medical instrument, the method comprising:
  providing a disposable container formed from a pulp material, the container including a base section comprising a base and an upstanding wall extending from the base, and a lid section configured to close the base section;

following use of said medical instrument, placing the contaminated medical instrument in the base section of the container;

closing the base section with the lid to enclose the instrument within the container; and transporting the instrument within the container away from the location of use.

In accordance with this method the contaminated instrument is enclosed and protected within the container during transit. The container protects the instrument from damage during transit as well as preventing the spread of contaminants from the instruments. As the container is formed from a pulp material it is able to be disposed of once the instrument is received at the Sterile Processing Department, thereby obviating the requirement to wash, sterilise or otherwise process the container.

The method may further comprise applying a cleaning solution to the instrument while it is contained within the base section, prior to closing the base section.

The cleaning solution may comprise a surfactant.

Preferably at least the base section includes a surfactant proof barrier on at least the inner surface of the pulp material to protect the base section from the cleaning solution.

Preferably the container is formed from a thermoformed pulp material.

BRIEF DESCRIPTION OF THE DRAWINGS

The present invention will now be described by way of example only with reference to the following illustrative figures in which:

Referring to FIG. 1, a container 1 for surgical instruments comprises a container body 2 and a lid 4. The container body 2 comprises a base 6 and upstanding walls 8 *a-d* defining an open enclosure. The body 2 and lid 4 are connected along a common edge 10 corresponding to the edge 8 *b* of the body 2, by a hinge 12. The body 2 and lid 4 are formed as a single piece from a moulded pulp material and the hinge 12 is a living hinge integrally moulded with the body 2 and lid 4.

Figure 1:
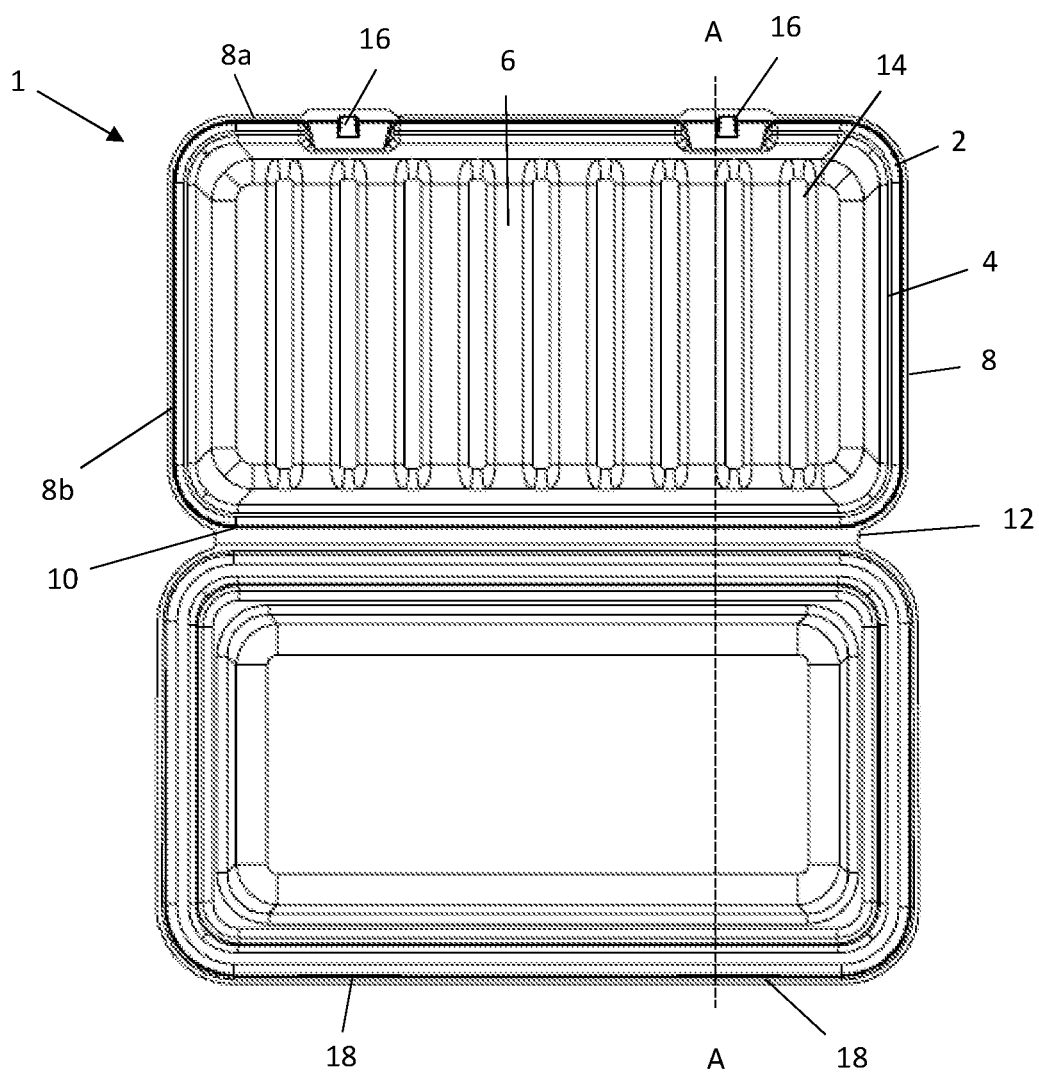
FIG. 1 shows a plans and side view of a container according to an embodiment of the invention.
Figure 1:
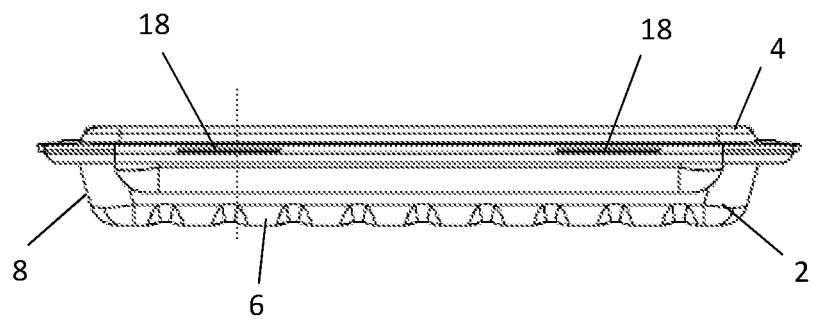

A series of spaced corrugated ridges 14 extend across the width of the base 6 between the side walls 8*a* and 8*b*. The ridges re-inforce the base and provide impact absorption for an instrument support on the base 2.

A pair of tabs 16 project from the upper edge of the outer side wall 8*a* of the base 2. The lid 4 includes a pair of corresponding slots 18 arranged to receive the tabs 16. The tabs 16 and slots 18 define a catch arrangement for holding the lid 4 in the closed position.

Figure 2:
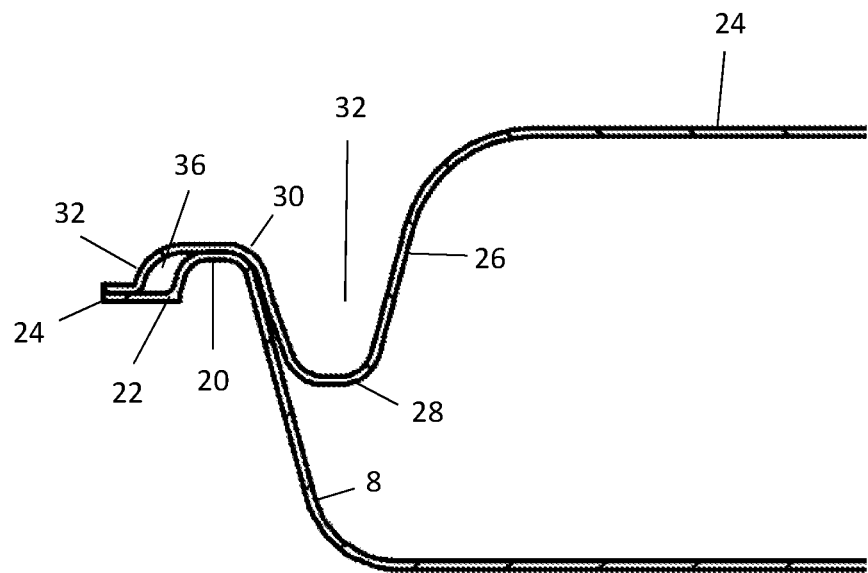
FIG. 2 shows a section view of an enclosure according to an embodiment of the invention.

The lid 4 and body 2 form a clamshell arrangement, with the hinged lid fitting over the upper edge of the body 2 to close the container. As shown in FIG. 2 the walls 8 taper outwardly in the upwards direction. At their upper edge the walls 8*a-d* curve outwardly and downwardly defining a curved upper lip 20 having a downwardly extending portion 22 at the end of the lip 20 that is spaced outwardly from the adjacent wall 8. A flange 24 extends horizontally outwards from the lower end of the lip 20. The lid 4 includes a roof 24 and an inner wall 26 extending downwardly from the roof 24. At the lower end 28 of the inner wall 26 the lid 4 curves upwardly defining an outer wall 30. The outer wall 30 is spaced outwardly from the inner wall 26 with a channel 32 being defined therebetween. The inner wall 26 extends downwardly to a depth whereby the lower end of the inner wall 26 is below the height of the upper lip 20 of the body 2 when the lid 4 is closed.

The inner wall 26 tapers outwardly in the downward direction towards the lower edge 28. The outer wall 30 tapers outwardly in the upward direction towards the lip 32 at the same angle as the walls 8. Hence the outer wall 30 is configured to seat parallel against the inner surface of the adjacent wall 8 of the body 2. The outer wall 30 extends upwardly to the height of the upper lip 20 and curves over and conforms to the shape of the inner edge of the lip 20. The lid 4 then curves downwardly defining an outer lip 32 that is spaced outwardly of the outer edge of the lip 20. A flange 34 extends outwardly from the lower edge of the lip 32 and is arranged to seat on the flange 24 of the body 2, the flange 34 of the lid extending outwardly the same distance as the flange 24 of the body, such that the lid 4 and body 2 have the same peripheral shape. A channel 36 is defined between the downwardly extending lip 32 and the outer wall 30 with the lip 32 defining the outer wall of the channel and the outer wall 30 defining the inner wall of the channel 36. The lip 20 of the body is received within the channel 36.

Figure 3:
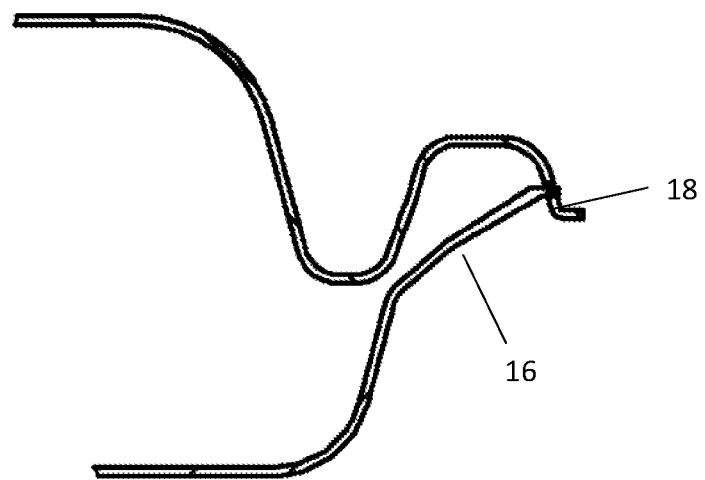
FIG. 3 shows a section view off an enclosure according to an embodiment of the invention.

The upper surface of the lip 20 seats against the inner surface of the channel 36. The outer wall 30 is configured to nest closely against the wall 8 in a tight push fit arrangement. As shown in FIG. 3, the tabs 16 extend outwardly from the outer wall 8*a* of the body 2 in an upwardly inclined angle to a height above the flanges 24 and 34 to the height of the slot 18 formed in the outer wall defining the lip 32. A horizontal locking portion 38 projects from the end of the tab 18 which inserts into the slot 18 to prevent the lid 4 from lifting upwardly thereby holding the lid 4 closed.

Figure 4:
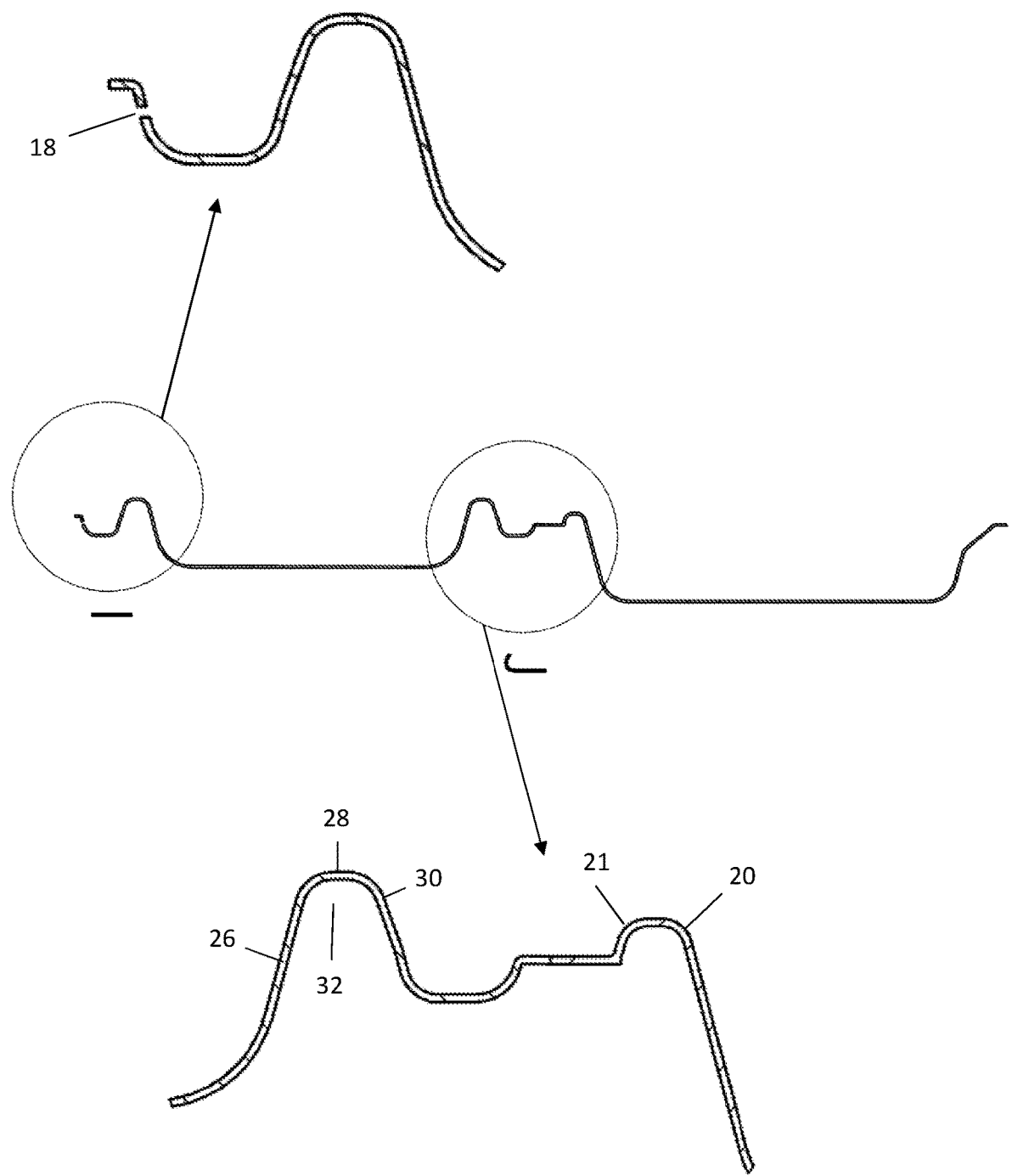
FIG. 4 is a section view through line A-A of FIG. 1.

FIG. 4 shows a cross section A-A of FIG. 1. The container 1 is moulded in the open position shown in FIG. 4 from a pulp fibre material. In this horizontal position it can be seen that the base 28 of the channel 32 defined by the inner wall 26 and outer wall 30 of the lid 4 extends to a greater height than the upper rim 21 of the lip 20, such that when the lid 4 is folded closed the base 28 is located below the upper rim 21. The heights of the inner wall 26 and outer wall 30 may be selected such that the base 28 of the channel 32 extends all the way to the base 6 where maximum security of the contents is required. The double walled arrangement formed by the inner 26 and outer 30 walls of the lid 4 provides lateral impact cushioning for the contents of the container, and well as effecting a secure closures and seal with the walls 8 of the body 2.

In use an instrument is selected from storage for use in the operating theatre and placed into a permeable sealed bag, such as a paper/plastic peel pouch bag that is able to withstand a sterilisation process such as high temperature steam sterilisation process as used in autoclaving, or sterilisation using a gas such as ETO (ethylene oxide). The sealed bag is then placed into a container 1. The container 1, including the bagged and sealed instrument is placed into a sterilisation unit such an autoclave chamber. The pulp fibre material of the container is gas permeable, meaning it allows the gas and/or steam to penetrate, and does not thermally shield the contents, ensuring that the instrument is properly exposed to the high temperature sterilisation environment. Once the sterilisation process has been completed the sterile instrument is housed within the container 1 and is kept from human contact and/or contact with other instruments during transport to the point of use within the operating theatre. The container thereby helps maintain sterility as well as preventing damage to the instrument.

Once the sterile instrument(s) has been placed in the container 1, the container 1 may be processed in one of the following ways at this stage:

i. A green tamper proof label indicating the instrument's "ready to use" condition is placed on the exterior of the container 1. A red label indicating the instrument's "soiled instrument" condition is placed inside the container 1 for later use.

ii. A green tamper proof label indicating the instrument's "ready to use" condition is placed on the exterior of the tray. The container 1 is then placed inside of a sterile peel pouch. A red label indicating the instrument's "soiled instrument" condition is placed inside the pouch for later use.

iii. A red label indicating the instrument's "soiled instrument" condition is placed inside the container 1 for later use. The container is then wrapped with an approved sterility wrap.

iv. The container 1 is placed inside of a wrapped tray or closed container system. In this case the container 1 is inside of a larger tray holding 70-90 instruments. The Single Cycle container 1 only holds a handful of the most delicate instruments.

The instrument is removed from the container 1 at the point of use. Following use the contaminated instrument may be returned to the container 1. An indicator is provided to indicate that the contents are used and contaminated. The indicator may be a sleeve, a sticker, a stamp or any other suitable means of indicating the state of the contents. Once the instrument has been placed within the container 1 a cleaning fluid is applied to the instrument to remove bulk contaminants and mitigate the impact of fluid drying on the instruments. The container 1 includes a surfactant proof barrier which prevents the surfactant solution from penetrating the pulp. The surfactant proof barrier may include a fluorocarbon. The fluorocarbon may be applied to the pulp within the slurry and/or may be applied to the pulp post-forming such as by spray application. The surfactant proof barrier may also or alternatively include a coating of surfactant proof resin. The surfactant proof resin is preferably applied to at least the inner surface of the base prior to thermoforming.

Following application of the cleaning fluid the lid 4 is closed to securely contain the instrument or instruments and a red tamper proof label is applied to the exterior of the tray to indicate that the instruments are contaminated and represent a biohazard. The tray is now in compliance to be transported through the hospital corridors. The instrument is transported for cleaning within the container 1 which prevents damage to the instrument during transit as well as preventing the spread of contaminants and preventing the risk of injury from the instruments. When the instrument is removed for cleaning on arrival at the Sterile Processing Department the container 1 may be disposed of, obviating the requirement for additional cleaning operations to clean and sterilise the container.

The invention claimed is:

1. A disposable container for surgical instruments, the container being formed from a moulded pulp material and comprising:
    an enclosure comprising a base and an upstanding wall extending from the base and tapering outwardly in an upwards direction towards its upper edge and a securing lip located at the upper edge of the upstanding wall;
    a lid configured to close the enclosure, the lid being hingedly connected to the upper edge of the upstanding wall;
    the lid includes a roof, an inner wall extending downwardly from the roof to a base, an outer wall extending upwardly from the base of the inner wall tapering outwardly away from the inner wall in the upwards direction at substantially the same angle as the upstanding wall of the enclosure, and a securing lip located at the upper end of the outer wall configured to secure over the securing lip of the enclosure, wherein when the lid and the enclosure are configured such that when the lid is in the closed position the base of the inner and outer walls is located within the enclosure at a position below the securing lip, a portion of the inner wall of the lid is located inwardly of the upstanding wall with the inner and outer walls forming a double walled arrangement inwardly of the upstanding wall for providing lateral cushioning to contents of the enclosure in use, with the outer wall being seated against the inner surface of the upstanding wall of the enclosure.

2. The disposable container according to claim 1, wherein the lid and the enclosure are integrally moulded.

3. The disposable container according to claim 2, wherein the hinge is integrally moulded with the lid and the enclosure.

4. The disposable container according to claim 1, wherein the inner wall tapers outwardly away in a downwards direction towards its base.

5. The disposable container according to claim 1, wherein the upstanding wall curves downwardly in an outwards direction at its upper edge to define the securing lip.

6. The disposable container according to claim 5, wherein a flange extends horizontally outwards from the distal end of the securing lip of the enclosure.

7. The disposable container according to claim 6, wherein a flange extends horizontally outwards from the distal end of the securing lip of the lid and is arranged to seat on top of the flange of the enclosure when the lid is closed.

8. The disposable container according to claim 1, wherein the enclosure is formed from a gas permeable material.

9. The disposable container according to claim 1, further comprising at least one locking tab extending from the upstanding wall of the enclosure, and the securing lip of the lid includes a corresponding slot arranged to receive the at least one locking tab when the lid is closed.

10. A method of sterilising a surgical instrument comprising:
    sealing a surgical instrument within a sterilising bag;
    placing the sterilising bag containing the instrument within a disposable container, the disposable container being formed from a moulded pulp material and comprising;
    an enclosure comprising a base and an upstanding wall extending from the base and tapering outwardly an upwards direction towards its upper edge and a securing lip located at the upper edge of the upstanding wall;
    a lid configured to close the enclosure, the lid being hingedly connected to the upper edge of the upstanding wall;
    the lid includes a roof, an inner wall extending downwardly from the roof to a base, an outer wall extending upwardly from the base of the inner wall tapering outwardly away from the inner wall in the upwards direction at substantially the same angle as the upstanding wall of the enclosure, and a securing lip located at the upper end of the outer wall configured to secure over the securing lip of the enclosure, wherein when the lid and the enclosure are configured such that when the lid is in the closed position the base of the inner and outer walls is located within the enclosure at a position below the securing lip, a portion of the inner wall of the lid is located inwardly of the upstanding wall with the inner and outer walls forming a double walled arrangement inwardly of the upstanding wall for providing lateral cushioning to contents of the enclosure in use, with the outer wall being seated against the inner surface of the upstanding wall of the enclosure; and placing the enclosure containing the instrument into a steriliser and exposing the enclosure to a sterilising gas such that said gas permeates the enclosure and sterilises the instrument contained therein.

11. The method according to claim 10, wherein the enclosure is closed when the instrument is placed and the enclosure is placed into the steriliser in the closed condition.

12. The method according to claim 10, wherein the sterilised instrument is transported to a point of use within the closed enclosure.

13. The method according to claim 12, further comprising returning the instrument to the enclosure following use and providing the enclosure with an indicia indicating the contents of the enclosure are contaminated.

\* \* \* \* \*